Figure 1:
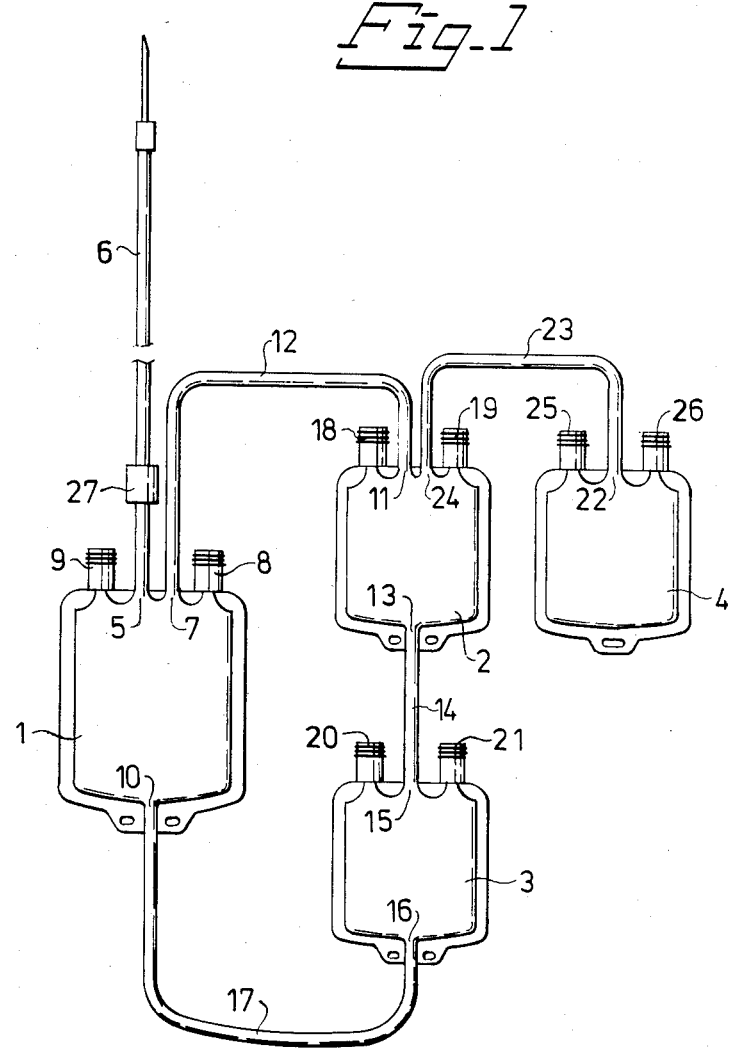

United States Patent [19]

Johansson et al.

[11] Patent Number: 4,608,178

[45] Date of Patent: Aug. 26, 1986

[54] METHOD OF SEPARATING BLOOD COMPONENTS

[76] Inventors: Anne S. Johansson, Vråkvägen 7A, S-752 52 Uppsala; Claes F. Högman, Statarvägen 14, S-752 45 Uppsala, both of Sweden

[21] Appl. No.: 683,566

[22] Filed: Dec. 19, 1984

Related U.S. Application Data

[63] Continuation of Ser. No. 423,244, Sep. 24, 1982, abandoned, which is a continuation of Ser. No. 133,868, Mar. 25, 1980, abandoned.

[30] Foreign Application Priority Data

Mar. 28, 1979 [SE] Sweden .............................. 7902761

[51] Int. Cl.[4] ........................................... B01D 21/26
[52] U.S. Cl. .................................. 210/744; 210/927; 222/1; 222/478; 422/44; 422/101; 494/37
[58] Field of Search ............... 210/744, 745, 767, 781, 210/782, 787, 789, 927; 422/41, 44, 101; 128/637, 762, 767; 222/1, 52, 64, 96, 103, 478; 494/21, 37

[56] References Cited

U.S. PATENT DOCUMENTS

| | | | |
|---|---|---|---|
| 3,044,663 | 7/1962 | Norton et al. | 222/64 X |
| 3,064,647 | 11/1962 | Earl | 233/26 X |
| 3,911,918 | 10/1975 | Turner | 422/44 X |
| 4,040,959 | 8/1977 | Berman et al. | 210/782 |

Primary Examiner—David Sadowski
Attorney, Agent, or Firm—Burns, Doane, Swecker & Mathis

[57] ABSTRACT

The invention relates to a method and a blood bag system for the separation of blood components from whole blood, the blood being tapped into a blood bag, which is then centrifugated to form an upper layer containing blood plasma, a lower layer containing red blood cells and an intermediate buffy coat layer, and it is characterized in that the blood is tapped into a first blood bag (1,28) having outlets both at the top (7,30) and at the bottom (1,33), and that after centrifugation the layer containing blood plasma is pressed out through the upper outlet (7,30) of the blood bag while the layer containing red blood cells is pressed out through the lower outlet port (10,33) of the blood bag, so that substantially only the intermediate layer remains in the bag (1,28).

8 Claims, 2 Drawing Figures

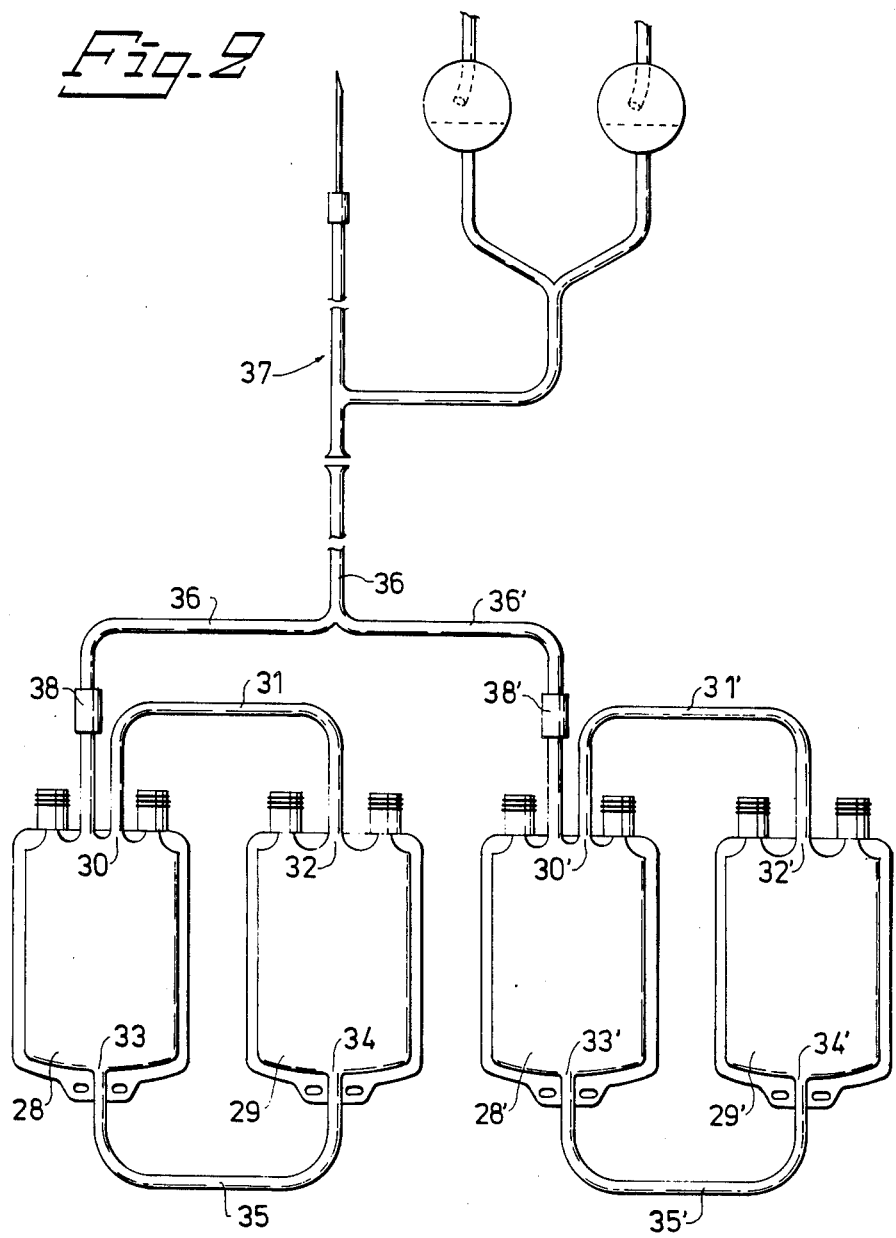

METHOD OF SEPARATING BLOOD COMPONENTS

This application is a continuation of application Ser. No. 423,244, filed Sept. 24, 1982, now abandoned, which is a continuation of Ser. No. 133,868, filed Mar. 25, 1980, now abandoned.

The present invention relates to an improved method of collecting, separating and storing blood components. The invention also relates to a blood bag system for use in this connection.

When collecting blood from a donor the cell components of the whole blood are usually separated from the plasma portion prior to storage and use. The separation is performed by sedimentation or, most frequently, by centrifugation, which yields an upper plasma layer, a thinner intermediate so-called buffy coat layer containing white blood cells and possibly thrombocytes, and a lower layer of red blood cells. A number of various methods and devices for collection, separation and storage of the blood components are known. In the presently most frequently used method a closed sterile blood bag system of the well known "Fenwal"-type is utilized. This system usually comprises a relatively large collecting bag and one or more transfer bags, which through connection tubes are connected to an outlet provided in the upper part of the collecting bag. After tapping of the blood to the collecting bag via a tapping tube, which also opens in the upper part of the bag, the collecting bag is centrifugated together with the transfer bag or bags, the collecting bag then being placed in a device for squeezing out the blood components. A simple and frequently used device of this kind consists of a vertical plate having a pressure plate pivotally journalled thereto, the latter being spring biased against the vertical plate. Thus, in order to squeeze out the contents of the collecting bag the bag is placed between the vertical plate and the spring biased pressure plate, blood plasma being pressed out through the outlet opening to one of the transfer bags via the connecting tube. The connecting tube to a possibly present second transfer bag is kept closed. When the buffy coat layer has reached the top edge of the collecting bag, the connection to the transfer bag with blood plasma is closed and the buffy coat layer is pressed out to the second transfer bag (after the tube connection has been opened) or the buffy coat layer is taken out through the tapping tube (which, however, may involve a contamination risk since the system then is not completely closed). Since the buffy coat layer has a tendency to stick to the bag walls, it is in most cases necessary to assist in the squeezing operation using the fingers. After the buffy coat layer has been squeezed out as much as possible the compression is interrupted, the blood plasma then being in one of the transfer bags, the red blood cells in the collecting bag and the buffy coat layer in the second transfer bag or other container.

The above described method has several disadvantages. Thus, squeezing out the blood components occupies the laboratory staff for a comparatively long time, since the squeezing operation must be monitored continuously and the squeezing of the buffy coat layer also requires manual assistance. Further, it is in practice only possible to get out 50 to 60% of the white blood cells due to the above mentioned adherence to the bag walls. A more automatized squeezing method is therefore desirable. The presently used blood bag systems and squeezing devices are, however, difficult to make more automatic. According to the invention there is therefore suggested an improved procedure using a modified blood bag system for eliminating the above mentioned disadvantages.

A basic concept of the invention is that whole blood is tapped to a collecting bag having outlets both at the top and at the bottom, and that, after centrifugation, the blood plasma is pressed out through the upper outlet and the red blood cells through the lower outlet while keeping the buffy coat layer in the collecting bag. Hereby a system is obtained, which is suitable for automation and simultaneously results in a considerably improved separation of the white blood cells.

Simple automation is made possible in that blood plasma and red blood cells can be pressed out simultaneously through the upper and lower outlets respectively of the collecting bag. The collecting bag is then preferably squeezed by uniform compression along the whole bag area, e.g. between two vertical, substantially parallel plates. A suitable such device is described in more detail in the simultaneously filed Swedish Patent Application No. 7902760-3. Because the red blood cells have a greater viscosity than the plasma layer, the latter will leave the collecting bag faster than the red blood cells. Therefore, suitable means, e.g. a photocell, are provided for sensing when the blood cell layer has reached a suitable, predetermined level in the collecting bag, and said sensing device is made to activate shut-off means for the outlet tube from the top outlet of the collecting bag. The bag contents are then pressed out only through the lower outlet and are automatically stopped at a predetermined residual volume in the collecting bag, corresponding to the volume of the buffy coat layer plus a small volume of red blood cells. The interruption of the compression of the collecting bag can easily be achieved, e.g. by suitable preadjustable spacing means for the plates between which the collecting bag is compressed.

In a variant the sensing means (one or more photocells or the like) are positioned essentially at the level of the buffy coat layer already from the start of the squeezing operation, and the sensing means are arranged to maintain the buffy coat layer at essentially the same level during the entire squeezing operation. In this embodiment the sensing means will alternatingly shut off and open the top outlet of the blood bag in response to the movements of the buffy coat layer. Thus, the sensing means will shut off the top outlet (leaving the bottom outlet open) when the buffy coat layer moves upwards. Correspondingly, the sensing means will open the top outlet when the buffy coat layer falls below the sensed level. An important advantage obtained when using this embodiment is that there will be only insignificant contact between the red blood cells and the white blood cells sticking to the bag wall, resulting in a greater degree of purity of the separated red blood cell layer.

A blood bag system according to the invention therefore comprises a blood collecting bag having outlets both at the top and at the bottom, which outlets are connected to at least one additional blood bag via conduits which can be shut-off.

A suitable closed blood bag system for blood tapping/blood storage comprises a collecting bag and two possibly interconnected transfer bags. The bags are preferably coupled in "circle", i.e. such that each of the upper and lower outlets of the collecting bag is connected to a transfer bag, and that the two transfer bags are interconnected. Preferably, the upper outlet of the collecting bag is connected to the top portion of the first transfer bag, the bottom portion of this transfer bag is connected to the top portion of the second transfer bag, and the bottom portion of the last-mentioned transfer bag is connected to the lower outlet of the collecting bag. After collection of whole blood in the collecting bag the same is centrifugated in conventional manner together with the transfer bags. In order to squeeze out the blood components it is then only necessary to place the collecting bag in a suitable squeezing device operating automatically according to the above described principle, and to activate the compression mechanism. It is then possible to leave the apparatus, which automatically squeezes out the blood plasma layer to one of the transfer bags and the red blood cells to the other, with the buffy coat layer remaining in the collecting bag. The blood components separated into the different blood bags can then be used or stored as desired. A third transfer bag may optionally be connected to the transfer bag intended for the blood plasma, in case the primary centrifugation is adjusted such that the top layer consists of thrombocyte-rich plasma. After repeated centrifugation the plasma is squeezed into the third transfer bag, leaving a thrombocyte concentrate in the original plasma bag.

The method according to the invention can also advantageously be used for leucapheresis, wherein white blood cells are separated from the blood and the remainder is recycled to the patient. A blood bag system according to the invention used for this purpose suitably consists of two basically identical blood bags, the upper and lower outlets of one of the blood bags being connected to the corresponding outlets of the other. After collecting blood in one of the bags the two blood bags are centrifugated, whereupon the contents are squeezed out as above. Then only the buffy coat layer with the white blood cells remains in the collecting bag, whereas the blood plasma and the red blood cells have been transferred to the other blood bag. The buffy coat layer is then collected for further separation or direct use, while the contents of the second blood bag are retransfused to the patient. Since up to 95% of the white blood cells can be separated from the whole blood the required number of blood tappings is considerably reduced in comparison with conventional techniques. This, of course, is both labour-saving and more comfortable for the patient or the donor.

The above described blood bag system for leucapheresis having two blood bags connected in a closed circuit can also advantageously be used for plasmapheresis (wherein the blood plasma is separated from the other blood components) and thrombopheresis (wherein the thrombocytes are separated from the other blood components).

In order to avoid coagulation of the blood and to increase the shelf life the blood in on tapping mixed with a solution containing an anti-coagulant and a nutritent agent. Normally, this solution is present in the collecting bag from the start of the blood tapping. According to a preferred embodiment of the invention, however, at least the anti-coagulant is originally present in a transfer bag and is mixed with the blood in the collecting bag on tapping. By making the tapped blood meet a suitable amount of anti-coagulant, chosen with regard to the tapping flow and supplied by gravity or pumping, a more gentle treatment of the blood components is obtained.

The method and the blood bag system according to the invention will now be described more in detail with reference to some special embodiments thereof in connection with the accompanying drawings, wherein FIG. 1 is a schematic representation of a blood bag system suitable for blood tapping and blood separation, and FIG. 2 is a schematic representation of a blood bag system suitable for use in leucapheresis, plasmapheresis and thrombapheresis.

The blood bag system shown in FIG. 1 comprises a collecting bag 1, two transfer bags 2 and 3 and optionally a further transfer bag 4. The blood bag 1 is in conventional manner provided with an inlet port 5 for a cannulaequipped blood tapping tube 6, and upper outlet port 7 and, in the shown case, pierceable tube connections 8 and 9. According to the invention the collecting bag 1 is also provided with lower outlet port 10. The transfer bag 2 has an upper port 11, which through a tube 12 is connected to the upper port 7 of the collecting bag. Through a lower port 13 and a tube 14 the transfer bag 2 communicates with the transfer bag 3 by means of an upper port 15 of the latter. The transfer bag 3 is in turn connected to the lower port 10 of the collecting bag 1 via a lower port 16 and a tube 17. In the same way as the collecting bag 1 the transfer bags 2 and 3 are, in the shown case, provided with conventional pierceable tube connections 18, 19 and 20, 21 respectively. The optional third transfer bag 4 is via an upper port 22 and a tube 23 connected to an upper port 24 of the transfer bag 2. Also the transfer bag 4 is in the shown case provided with pierceable tube connections 25 and 26.

The above described blood bag sytsem for collection, separation and storage of blood components may e.g. be used in the following way. Blood is tapped to the collecting bag 1 through the tapping tube 6 in conventional manner. The tube connections 12, 14 and 17 and, when a third transfer bag 4 is used, also the tube connection 23 are then shut off, e.g. by a tube clamp. A sterile anticoagulant and nutrition solution can in conventional manner from the start be contained in the collecting bag, but according to the invention it is preferred that the anti-coagulant initially is in the transfer bag 2 for being fed into the collecting bag 1 through the conduit 12 by gravity or pumping simultaneously with the tapping of blood through the conduit 6. Since the blood which is tapped at the beginning of the process is not subjected to a large volume of the anti-coagulant solution, there will be achieved a considerably milder treatment of those components of the blood which can be adversely effected by too great amounts of such a solution is achieved. In this variant the tube connection 12 between the collecting bag 1 and the transfer bag 2 is, of course, open when tapping the blood. By actuating those portions of the tube conduits 6 and 12 which are closest to the collecting bag 1 by means of any suitable pumping device. e.g. a properly designed segment or peristaltic pump with different pumping speeds for the two conduits, a suitable mixed flow (e.g. 1:7) of blood and anti-coagulant containing solution from the transfer bag 2 to the collecting bag 1 can be obtained. The blood tapping tube 6 is in this case preferably provided with a "cushion" portion 27, which can be affected by the pressure of the blood flow and which is monitored by a pressure sensor. The latter then controls the pumping speeds, so that the pumping of blood and anti-coagulant corresponds to the blood flow through the conduit 6, while maintaining a constant mixing proportion of blood and anti-coagulant solution. By operating as described above when tapping the blood it is not necessary to agitate the collecting bag, e.g. by rocking as is usual in conventional blood tapping, for obtaining good mixing of the blood and the added solution.

After completed blood tapping the conduit 6 is shut off, e.g. by welding, and the conduit 12 is shut off temporarily by a tube clamp, whereupon the whole bag system is centrifugated to form in the collecting bag an upper layer of blood plasma (normally about 60% of the blood volume), an intermediate comparatively very thin layer containing white blood cells and possibly thrombocytes—the so-called buffy coat layer—and a lower layer mainly containing red blood cells. For separation of the layers the collecting bag is introduced into a suitable squeezing or pressing device to squeeze out the contents through the upper and lower ports 7 and 10. A suitable device is, as mentioned above, described in the simultaneously filed Swedish patent application No. 7902760-3. In this device the collecting bag is introduced between a vertical wall and a pressure plate, which is movable essentially perpendicularly thereto. The connecting conduits 12 and 17 are opened for passage of liquid, and the driving of the pressure plate, which is effected by suitable driving means, is activated. Blood plasma will then be pressed out from the collecting bag 1 via the tube conduit 12 to the transfer bag 2, and at the same time red blood cells are pressed out to the transfer bag 3 through the lower port 10 and the tube conduit 17. Because the layer of red blood cells has greater viscosity than the blood plasma the level of the red blood cells with slowly move upwards as the bag is compressed. For partial automation of the process the device is provided with e.g. a photocell, preferably provided on the pressure plate, sensing the upper level of the red blood cells in the collecting bag 1 when the same has reached such a level that substantially all blood plasma has been pressed out from the bag. The photocell is arranged to activate suitable shut-off means, such as a solenoid valve, blocking the connection between the collecting bag 1 and the transfer bag 2 by pinching the tube 12. The discharge from the collecting bag 1 then only takes place through the port 10 and the tube 17. The squeezing device is further preferably provided with appropriate means for preventing further compression of the collecting bag 1 when the lower level of the buffy coat layer approaches the port 10. This may e.g. be achieved by one or more pre-adjustable spacing means, which prevent further displacement of the pressure plate towards the wall portion when the volume of the collecting bag 1 corresponds to the volume of the buffy coat layer plus a marginal volume of red blood cells. After the means for compressing the collecting bag 1 have been activated, the operator can leave the device unattended, since the continued separation of blood components will be continued and completed automatically. A pre-requisite is of course that the transfer bag 3 is held in such a position that the liquid levels in the two bags are at approximately the same level when the separation is completed, since otherwise further discharge from the collecting bag can take place. Thus, after completed separation the blood plasma is in the transfer bag 2 and the red blood cells in the transfer bag 3, while the buffy coat layer remains in the collecting bag 1.

In an alternative embodiment of the above described automated procedure the photocell is positioned in the vicinity of the initial level of the buffy coat layer. As in the above embodiment the sensing means will shut off the connection between the collecting bag 1 and the transfer bag 2 when the buffy coat layer (or possibly the top level of the red blood cell layer) moves upwards and enters the level sensed by the sensing means. Conversely, the connection between the bags 1 and 2 will be re-opened when the buffy coat layer falls below the sensed level. As a result the buffy coat layer will move up and down past the photocell with a comparatively small amplitude of the movement. Thus, there will be a continuous flow from the collecting bag 1 to the transfer bag 3, and an intermittent flow from the said bag 1 to the transfer bag 2, the levels of the buffy coat layer and the red blood cell layer being essentially constant all the time. As a result only the uppermost portion of the red blood cell layer will get in contact with the white blood cells adhering to the wall of the bag. This in turn results in higher purity of the separated red blood cell layer.

As mentioned above the added nutrient solution, whose main function is to permit extended storage of the red blood cells, can initially be contained in the collecting bag 1, but this solution is preferably from the beginning contained in the transfer bag 3. In this manner the solution will not be diluted by the blood plasma, and the composition of the solution can be optimized for storage of red blood cells.

After completed separation as above the connection through the tubes 12 and 17 is blocked, e.g. by welding, and the collecting bag 1 is possibly separated from the transfer bags for storage or further processing of the blood components.

The above described blood bag system offers a high degree of flexibility. For instance, a thrombocyte concentrate may be prepared in the transfer bag 2 if the primary centrifugation is adjusted such that the upper layer will consist of thrombocyte rich plasma. After repeated centrifugation the plasma separated from the transfer bag 2 can be transferred to the third transfer bag 4 connected via the tube 23, whereby a closed system is obtained. Alternatively the plasma may be pressed out from the transfer bag 2 for industrial fractionation, e.g. through the inlet tube 12 or through the tube 23 without the transfer bag.

If the centrifugation is adjusted such that the transfer bag 2 after the separation contains cell-poor plasma, the latter can be separated, deep-frozen, and stored, suitably at temperatures below −50° C. The transfer bag 2 can also be maintained in association with the transfer bag 3. The twin-bag 2, 3 is then stored in a refrigerator with the tube connection 14 temporarily blocked, and it forms a system for the preparation of microaggregate-poor whole blood, if this should be desirable. The two bags can also at any time during the storage be separated for individual use or storage.

As mentioned above the transfer bag 3 preferably from the beginning contains substances for optimum storage of red blood cells. When preparing a thrombocyte-rich plasma as above, a suitable amount of this storage solution can, if desired, be transfered from the transfer bag 3 to the transfer bag 2 before the separation process is started. In this way it is possible to adjust the pH-value to a desired level in the transfer bag 2.

As appears from the above the novel method according to the invention is labour-saving by allowing partial automation of the separation process. A considerable advantage is further the high degree of separation of the white blood cells (about 95%) which can be achieved because the buffy coat layer is maintained in the collecting bag 1 during separation. This can be utilized in so-called leucapheresis, i.e. separation of white blood cells and thrombocytes from the blood, as described below in connection with FIG. 2.

The blood bag system for leucapheresis of FIG. 2 comprises as a basic unit two interconnected blood bags 28 and 29, whose design essentially corresponds to the blood bag 1 of FIG. 1. The blood bag 28 is via an upper port 30 and a connection tube 31 connected to a port 32 at the top of the blood bag 29. Similarly the bottom of the blood bag 28 is connected to the bottom of the blood bag 29 through lower ports 33 and 34 respectively and a connecting tube 35. The blood bag 28 is further provided with a blood tapping tube 36, opening at the top of the bag. For reasons explained further below the basic system is doubled, corresponding reference designations in the Figure being provided with prime marks. The reference numeral 37 indicates a combined tapping and transfusion assembly, which in a way known per se comprises a blood tapping cannula and a tube connection having a drip chamber for the introduction of electrolyte solution and re-transfusion of blood.

In use the double twin-bag system is connected to the tapping/transfusion assembly 37 via the blood tapping tube 36. The connecting conduit 35 between the two blood bags 28 and 29 as well as the connection 36' are initially shut off by means of a tube clamp or the like. As in the system shown in FIG. 1 a suitable amount of anti-coagulant solution is preferably placed in the blood bag 29 from the beginning. The anti-coagulant solution is then added continuously from the blood bag 29 to the blood bag 28 in the course of the tapping, conveniently by means of a tube pump as mentioned in connection with FIG. 1 (the reference numerals 38 and 38' indicate "pressure cushions" corresponding to 27 in FIG. 1).

After completion of the blood tapping the blood bag system 28, 29 is separated by sealing and cutting the tube 36 below the branching point thereof. The upper connection 31 between the bags 28 and 29 is shut off by means of a tube clamp, and the system is centrifugated. Similarly as above one obtains an upper plasma layer, an intermediate buffy coat layer and a lower layer with red blood cells. The components are squeezed out from the blood bag 28 in the same way as described above in connection with FIG. 1 after opening of the tube connections 31 and 35. Blood plasma and red blood cells are pressed over to the blood bag 29 through the upper and lower tube connections 31 and 35 respectively, while the buffy coat layer remains in the collecting bag 28. The intermediate cell layer remaining in the blood bag 28 is collected for further separation or for direct use, whereas the contents of the blood bag 29 is retransfused to the patient. Another tapping of blood is then performed in the same way using the blood bag system 28', 29'.

Thanks to the high degree of separation of the white blood cells the amount of blood to be tapped can be reduced considerably, which besides being labour-saving results in reduced strains on the patient or the blood donor.

The above described blood bag system can preferably also be used for such techniques as plasmapheresis and thrombapheresis. In the case of plasmapheresis blood tapping is made in the same way as above. After centrifugation there is obtained in the blood bag 29 an upper layer containing thrombocyte-poor plasma, an intermediate layer containing white blood cells and thrombocytes, and a lower layer, mainly comprised of red blood cells. During the squeezing procedure the lower tube connection 35 is blocked by means of a tube clamp or the like, so that blood plasma is transferred to the blood bag 29 via the upper tube connection 31, while the buffy coat layer and the red blood cells remain in the blood bag 28. The contents of the blood bag 28 are then transfused back into the blood donor.

In thrombapheresis blood tapping is made in the same way as in leucapheresis and plasmapheresis, followed by centrifugation to form an upper layer of thrombocyte-rich plasma. This upper layer is then pressed into the blood bag 29 in the same way as in the above described plasmapheresis process. After repeated centrifugation an upper layer of thrombocyte-poor plasma is obtained in the blood bag 29, and this plasma layer is then transferred from the blood bag 29 into the blood bag 28, after which the contents of the blood bag 28 are re-transfused to the patient or the blood donor.

An alternative thrombapheresis procedure is to start from the thrombocyte/leucocyte concentrate obtained in the above described leucapheresis and to separate the latter by centrifugation.

The method and the blood bag system according to the invention are, of course, not restricted to the above specially described and shown embodiments, but many variations and modifications are possible within the scope of the subsequent claims. This is especially true concerning the specific design of the individual blood bags, the number of tube connections, the design of the connecting tube systems, the temporary blocking of the tubes during the process, etc.

What we claim is:

1. A method of separating blood components contained in a blood sample, comprising the steps of:
   (a) providing a primary blood bag for receiving the blood sample;
   (b) providing at least two transfer blood bags and at least two conduits, a first of said at least two conduits connecting said primary bag with a first of said at least two transfer blood bags and a second of said at least two conduits connecting said primary bag with a second of said at least two transfer blood bags;
   (c) collecting a blood sample in the primary blood bag having at least one top portion outlet connecting with the first of said at least two conduits and at least one bottom portion outlet connecting with the second of said at least two conduits;
   (d) centrifugating said primary blood bag and said transfer blood bags for separating said blood sample into an upper layer containing blood plasma, a lower layer containing red blood cells, and an intermediate layer containing white blood cells; and
   (e) squeezing said primary bag while said intermediate layer is in fluid contact with each of said upper and lower layers in said primary bag to thereby cause said upper layer to transfer from said primary bag through said at least one top portion outlet and the first of said at least two conduits to said first transfer bag and said lower layer to transfer from said primary bag through said at least one bottom portion outlet and the second of said at least two conduits to said second transfer bag so as to leave essentially only said intermediate layer in said primary blood bag.

2. The method of claim 1, characterized by squeezing out said upper and lower layers through the respective outlet (7, 30; 10, 33) of the primary blood bag by compression of the latter over substantially an entire area thereof, and stopping the compression of the primary blood bag (1, 28) when a pre-determined residual volume remains in the primary blood bag (1, 28).

3. The method of claim 1 or 2, characterized by the step of controlling said transfer of said upper layer from said primary blood bag so as to maintain said intermediate layer essentially at the same level in the primary blood bag during said squeezing.

4. The method of claim 3, characterized by the steps of continuously sensing a predetermined level in said primary blood bag and in response thereto closing said at least one top portion outlet when said intermediate layer, or a top portion of said lower layer, reaches said predetermined level, and opening said at least one top portion outlet when said intermediate layer, or a top portion of said lower layer, falls below said pre-determined level.

5. The method of claim 1 or 2, characterized by stopping flow of said upper layer when said intermediate layer, or top portion of said lower layer, has reached a pre-determined level, and continuing squeezing out of said lower layer until a pre-determined residual volume remains in said primary blood bag (1, 28).

6. The method of claim 5, characterized by simultaneously adding an anti-coagulant to the blood sample with said collecting of said blood sample in said primary blood bag, said anti-coagulant being supplied from a separate bag connected to said primary blood bag.

7. The method of claim 1, characterized by simultaneously adding an anti-coagulant to the blood sample with said collecting of said blood sample in said primary blood bag, said anti-coagulant being supplied from a separate bag connected to said primary blood bag.

8. A method of separating blood components contained in a blood sample, comprising the steps of:
   (a) providing a primary blood bag for receiving the blood sample;
   (b) providing a common blood bag and at least two conduits, a first of said at least two conduits connecting said primary bag with said common blood bag and a second of said at least two conduits connecting said primary bag with said common blood bag;
   (c) collecting a blood sample in the primary blood bag having at least one top portion outlet connecting with the first of said at least two conduits and at least one bottom portion outlet connecting with the second of said at least two conduits;
   (d) centrifugating said primary blood bag and said common blood bag for separating said blood sample into an upper layer containing blood plasma, a lower layer containing red blood cells and an intermediate layer containing white blood cells;
   (e) squeezing said primary bag while said intermediate layer is in fluid contact with each of said upper and lower layers in said primary bag to thereby cause said upper layer to transfer from said primary bag through said at least one top portion outlet and the first of said at least two conduits to said common blood bag and said lower layer to transfer from said primary bag through said at least one bottom portion outlet and the second of said at least two conduits to said common blood bag so as to leave essentially only said intermediate layer in said primary blood bag.

* * * * *